US007524834B2

(12) United States Patent
Karlsson et al.

(10) Patent No.: US 7,524,834 B2
(45) Date of Patent: Apr. 28, 2009

(54) STERILE POWDERS, FORMULATIONS, AND METHODS FOR PRODUCING THE SAME

(75) Inventors: Ann-Kristin Karlsson, Staffanstorp (SE); Cheryl Larrivee-Elkins, Framingham, MA (US); Ove Molin, Huddinge (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 09/993,669

(22) Filed: Nov. 27, 2001

(65) Prior Publication Data

US 2002/0065256 A1    May 30, 2002

Related U.S. Application Data

(63) Continuation of application No. 09/230,781, filed as application No. PCT/SE98/02039 on Nov. 11, 1998, now Pat. No. 6,392,036.

(30) Foreign Application Priority Data

Nov. 14, 1997   (SE) .................................. 9704186

(51) Int. Cl.
*A61K 31/58* (2006.01)
*C07J 53/00* (2006.01)
(52) U.S. Cl. ...................... 514/174; 540/100
(58) Field of Classification Search ................ 424/489; 540/63, 120; 514/169, 174, 177–182
See application file for complete search history.

(56) References Cited

U.S. PATENT DOCUMENTS

| 3,962,430 | A |   | 6/1976  | O'Neill ....................... 424/185 |
|-----------|---|---|---------|----------------------------------------|
| 3,992,534 | A | * | 11/1976 | Brattsand et al. ............ 514/174   |
| 5,192,528 | A |   | 3/1993  | Radhakrishman et al.                   |
| 5,540,930 | A | * | 7/1996  | Guy et al. .................... 424/427 |
| 5,556,964 | A |   | 9/1996  | Hofstraat et al.                       |
| 5,824,668 | A | * | 10/1998 | Rubinfeld et al. ........... 514/170    |
| 5,837,699 | A |   | 11/1998 | Sequeira et al.                        |
| 6,066,292 | A |   | 5/2000  | Purwar                                 |
| 6,187,765 | B1 | * | 2/2001 | Harris et al. ................. 514/172  |
| 6,241,969 | B1 | * | 6/2001 | Saidi et al. .................... 424/45 |
| 2005/0089476 | A1 |   | 4/2005 | Ronchi et al.                       |
| 2005/0201888 | A1 |   | 9/2005 | Amar et al.                          |

FOREIGN PATENT DOCUMENTS

| EP | 1033991 B1   |   | 4/2002  |
|----|--------------|---|---------|
| JP | 57-032212    |   | 2/1982  |
| JP | 62-114917    |   | 5/1987  |
| PT | 69652        |   | 1/1979  |
| WO | WO 92/11280  |   | 7/1992  |
| WO | WO 95/31964  |   | 11/1995 |
| WO | WO 96/09814  |   | 4/1996  |
| WO | WO 96/32095  |   | 10/1996 |
| WO | WO 97/01341  | * | 1/1997  |
| WO | WO 03/070285 A1 |   | 8/2003 |
| WO | WO 2004/054545 A1 |   | 7/2004 |

OTHER PUBLICATIONS

Illum, L. et al "Surface area stability of micronized steroids sterilized by irradiation" Arch. Pharm. Chemi Sci. Ed. 2, pp. 167-174, 1974.*
Bussey, D. et al "Sterilization of corticosteroids by 60-Co irradiation" J. Pharm. Parenter. Sci. Tech. vol. 37, No. 2, pp. 51-54.*
Ansel, H. et al "Pharmaceutical Dosage Forms and Drug Delivery Systems" 6th edition (1995) Williams & Wilkins (pub) pp. 294 298.*
Jonsson, G. et al "Budesonide is metabolized by cytochrome P450 . . . " Drug Metab. Dep. (1995) vol. 23, No. 1, pp. 137-142.*
Morice, A. et al "A comparison of nebulized budesonide with oral prednisolone in the treatment of exacerbations of obstructive pulmonary disease" Clin. Pharmacol. Ther. (1996) vol. 60, pp. 675-678. (abstract only).*
Day, J. et al. "Budesonide aqueous nasal spray and pressurized metered dose . . . " (1997) Am. J. Rhinol. vol. 11, No. 1, pp. 77-83. (abstract only).*
Jones, A. et al "Pulmicort Turbohaler once daily as initial prophylactic therapy . . . " (1994) Respir. Med. (1994) vol. 88, pp. 293-299.*
Crompton, G. "The adult patient's difficulties with inhalers" (1990) Lung, suppl: 658-662.*
Monthly Prescribing Reference: "Rhinocort Aqua" http://formularyreference.com/monograph/show/d/3269 accessed online Feb. 29, 2008.*
Kane, M. P. et al., "Radolytic degradation of scheme for 60Co-irradiated corticosteroids", J. Pharm. Sci. vol. 72, No. 1, pp. 30-35, 1983.
Ansel, H. et al., "Pharmaceutical Dosage Forms and Drug Delivery Systems", 6th edition, Williams & Wilkins, pp. 294-299, 1995.
Ernst et al., "Sterilization with Gaseous Ethylene Oxide: A Review of Chemical and Physical Factors", Biotechnology and Bioengineering, vol. X, pp. 1-31 (1968).
"Ethylene Oxide, Ethylene Chlorohydrin, and Ethylene Glycol", Federal Register, vol. 43(122), Department of Health, Education, and Welfare, pp. 27474-27483 (1978).
European Agency for the Evaluation of Medicinal Products, "Guidelines Medicinal products for human use, Quality and biotechnology", pp. 11-22 (1998).
Gilbert et al., "Effect of Moisture on Ethylene Oxide Sterilization", Applied Microbiology, vol. 12(6), pp. 496-503 (1964).
Guide to Inspections of Sterile Drug Substance Manufacturers, http://fda.gov/org/inspect_ref/igs/subst.html, pp. 1-7 (1994).

(Continued)

*Primary Examiner*—Leigh C Maier
(74) *Attorney, Agent, or Firm*—Fish & Richardson P.C.

(57) ABSTRACT

The invention provides sterile glucocorticosteroids and sterile formulations containing glucocorticosteroid and use thereof in the treatment of an allergic and/or inflammatory condition of the nose or the lungs.

85 Claims, No Drawings

OTHER PUBLICATIONS

Mullican et al., "Dry Heat or Gaseous Chemical Resistance of *Bacillus subtilis* var. *niger* Spores Included Within Water-soluble Crystals", Applied Microbiology, vol. 16, pp. 1110-1113 (1968).

Prescott et al., Microbiology, pp. 237-246 (1990).

Product description for Rhinocort Aqua® (budesonide), Nasal Spray 32 mcg, 2 pages, dated Jan. 2005.

Pulmicort Turbuhaler® (budesonide inhalation powder), 4 pages, dated Oct. 2006.

Astra Draco Specification for micronized budesonide prepared for use in the Rhinocort Aqua® nasal spray product, 2 pages, dated Nov. 20, 1995.

Astra Draco Specification for budesonide prepared for use in the Pulmicort Turbuhaler® product, 2 pages, dated Apr. 1, 1997.

US Pharmacopeia 23/NF18, pp. 1686-1690 and 1963-1975, published by United States Pharmacopeial Convention, Inc., Rockville, MD (1995).

Specification for Pulmicort Respules®, 3 pages, GEL Version ID: RITA.000-243-420.3.0, printed on Jun. 15, 2008.

US Pharmacopeia 23, "Microbial Limit Tests" USP <61>, pp. 1681-1686, published by United States Pharmacopeial Convention, Inc., Rockville, MD (1995).

Astra Draco Specification for Pulmicort 200 Turbuhaler®, 5 pages, dated Sep. 17, 1997.

Astra Draco Specification for Rhinocort® nasal spray, 1 page, dated 04/225/91.

"Guidance for Industry: Sterility Requirement for Aqueous-Based Drug Products for Oral Inhalation—Small Entity Compliance Guide," U.S. Department of Health and Human Services, Food and Drug Administration, Center for Drug Evaluation and Research (CDER), 4 pages, Nov. 2001.

Pulmicort Respules® (budesonide inhalation suspension) product information, 6 pages, dated Jun. 2007.

Astra Draco Specification for Pulmicort® suspension for Nebulizing product, 2 pages, dated Feb. 23, 1994.

Recorded minutes of a Nov. 20, 1996 pre-NDA meeting attended by Astra USA, Astra Draco, and FDA officials, 6 pages.

Astra Draco Specification for "budesonide micronized sterile", 2 pages, dated Nov. 18, 1983.

Astra Draco documentation (in Swedish) of Manufacturing Method for Preferid® cream dated Sep. 9, 1980, 5 pages, and English translation, 5 pages.

Internal Astra Draco document "Establishment of limits for content and related foreign steroids in budesonide substance" dated Mar. 26, 1980, 5 pages.

Internal Astra Draco document "Limits for content and related foreign steroids in budesonide substance," dated Nov. 4, 1980.

Internal Astra Draco document "Analytical Certificate", dated Aug. 28, 1980, in Swedish, 1 page, with English translation, 1 page.

Internal Astra Draco document "Analytical Certificate", dated Sep. 14, 1978, in Swedish, 1 page, with English translation, 1 page.

Internal Astra Draco document "Analytical Certificate", dated Feb. 28, 1980, in Swedish, 1 page, with English translation, 1 page.

Internal Astra Draco document "Analytical Certificate", dated Mar. 28, 1980, in Swedish, 1 page, with English translation, 1 page.

Internal Astra Draco document "Analytical Certificate", dated Jun. 9, 1980, in Swedish, 1 page, with English translation, 1 page.

Internal Astra Draco document "Analytical Certificate", dated May 4, 1979, in Swedish, 1 page, with English translation, 1 page.

Internal Astra Draco document "Analytical Certificate", dated May 8, 1979, in Swedish, 1 page, with English translation, 1 page.

Internal Astra Draco document "Analytical Certificate", dated Dec. 12, 1978, in Swedish, 1 page, with English translation, 1 page.

* cited by examiner

STERILE POWDERS, FORMULATIONS, AND METHODS FOR PRODUCING THE SAME

CROSS REFERENCE TO RELATED APPLICATIONS

This application is a continuation of U.S. Ser. No. 09/230,781, filed Jan. 29, 1999 (now U.S. Pat. No. 6,392,036), which is the National Stage application of International Application No. PCT/SE98/02039, filed Nov. 11, 1998, which claims the benefit of Swedish Patent Application No. 9704186-7, filed Nov. 14, 1997. The contents of these applications are incorporated herein by reference in their entirety.

FIELD OF THE INVENTION

This invention relates to a process for sterilization of a powerderd form of a glucocortico-steriod, sterile glucocorticosteroids, sterile formulations containing glucocorticosteroids and use thereof in the treatment of an allergic and/or inflammatory condition of the nose or lungs.

BACKGROUND OF THE INVENTION

Various methods have been proposed in the past for the sterilization of glucocorticosteroids. PT-A-69652 discloses the cold sterilization of micronized glucocorticosteroids using mixtures of ethylene oxide and carbon dioxide, since, according to PT-A-69652, steroids in powder form are not stable at temperatures above 60° C. Specific examples of glucorticosteroids are prednacindone, dexamethasone and prednisolone, and salts, esters and fluoro derivatives thereof, including dexamethasone acetate, dexamethasone phosphate, prednisolone pivalate and 9-alphafluoro prednisolone. However, ethylene oxide is toxic and when it is used to sterilize glucocorticosteroids it has been found that the residual amounts of the ethylene oxide contravene pharmaceutical guidelines which require very low levels of residual ethylene oxide. Accordingly this method has been found to be unsuitable for producing therapeutically acceptable glucocorticosteroids and formulations thereof.

U.S. Pat. No. 3,962,430 discloses a method for the production of sterile isotonic solutions of medicinal agents, which comprises adding the agent to a saturated solution of sodium chloride in water at 100° C. and then heating the mixture at 100-130° C. This method is not suitable for suspensions of fine particles of glucocorticosteroids which are intended for inhalation because the water, and the heating and cooling involved, produce unfavorable changes in the size of the particles. Indeed it can lead to the formation of bridges between the fine particles producing large, hard aggregates which will not deaggregate into the desired fine particles upon administration.

A putative alternative is dry heat sterilization. According to the European Pharmacopoeia (1996, pp. 283-4) a normal heat sterilization process runs at 180° C. for 30 min or at a minimum of 160° C. for at least 2 hours. According to Pharmacopoeia Nordica (1964, pp. 16) such a sterilization can be carried out at 140° C. for 3 hours. However at the temperatures of these processes glucocorticosteroids suffer significant degradation and are subject to changes in their surface structure.

Sterilization by β- or γ-irradiation is also known. Indeed Illum and Moeller in Arch. Pharm. Chemi. Sci., Ed. 2, 1974, pp. 167-174 recommend the use of such irradiation to sterilize glucocorticosteroids. However when such irradiation is used to sterilize certain finely divided, e.g. micronized, glucocorticosteroids, they are significantly degraded.

WO-A-96/09814 to Andaris Ltd. relates to spray-dried particles of a water-soluble material with a mass median particle size of 1 to 10 μm. The aim of the invention is to produce uniform and reproducible particles for use in dry powder inhalers. The water-soluble material is preferably a human protein or a fragment thereof, in natural or recombinant form, e.g. human serum albumin (HSA), alpha-1 antitrypsin or alcohol dehydrogenase. Also combinations of an active material with a carrier were produced e.g. budesonide and lactose. It is stated generally that the microparticles produced can be sterile without teaching how this could or would be achieved nor showing any proof thereof.

WO-A-96/32095 to Astra AB relates to a process for the preparation of respirable particles by dissolving an inhalation compound in a solvent, introducing the resulting solution containing the inhalation compound in droplet form or as a jet stream into an anti-solvent which is miscible with the solvent and which is under agitation. Budesonide with a mass median diameter (MMD) of less than 10 μm is produced with the process. There is no information in WO-A-96/32095 about sterilization or sterile particles.

WO-A-92/11280 to Instytut Farmaceutyczny relates to a method of obtaining (22R) diastereoisomer of budesonide by a condensation reaction followed by crystallizing the crude product of condensation from ethanol. The obtained 21-acetate of budesonide (22R) is hydrolyzed and the product thus obtained is crystallized from ethyl acetate. The content of (22S) diastereoisomer of budesonide is 1% or less. There is no information in WO-A-92/11280 about sterilization or sterile particles.

We have also found that attempts at terminal sterilization of the pharmaceutical formulations, especially suspensions, e.g. aqueous suspensions, of glucocorticosteroids have all proved unsatisfactory. Such suspensions can not normally be sterilized by sterile filtration as most of the particles of glucocorticosteroid will be retained on the filter. We have also shown that moist heat sterilization, e.g. steam treatment of glass vials containing the product, leads to an unacceptable change in particle size.

Various aqueous suspensions of finely divided glucocorticosteroids are known, e.g. the budesonide-containing product known as Pulmicort® nebulising suspension. (Pulmicort® is a trademark of Astra AB of Sweden). Similar formulations of fluticasone propionate are known from WO-A-95/31964.

Accordingly a new process for the sterilization of glucocorticosteroids (and formulations containing them) is required.

Surprisingly we have now found that effective sterilization of dry glucocorticosteroids can be carried out at a significantly lower temperature than that considered necessary for the heat sterilization of other substances. Such sterile glucocorticosteroids can be used in the preparation of sterile formulations containing them.

DESCRIPTION OF THE INVENTION

According to the invention there is provided a process for the sterilization of a glucocorticosteroid, which process comprises heat treating the glucocorticosteroid in the form of a powder at a temperature of from 100 to 130° C. The process is preferably carried out at a temperature of from 110 to 120° C., more preferably at about 110° C., preferably for up to about 24 hours, more preferable up to 10 hours, e.g. from 1 to 10 hours. The process is conveniently carried out under atmospheric conditions, i.e. in air, but may also be carried out under an inert gas atmosphere, e.g. an atmosphere of argon or nitrogen.

Surprisingly we have found that this process kills many more spores when applied to the glucocorticosteroid budesonide than when applied to the comparison substance calcium stearate. Even better results were obtained with the glucocorticosteroid rofleponide.

It is believed, but we do not intend to be limited by this explanation, that the unexpectedly low temperature at which the glucocorticosteroids can be sterilized indicates that the glucocorticosteroid may provide some synergistic effect, when taken together with the heat treatment, in destroying the spores.

The glucocorticosteroid used in the invention is preferably an anti-inflammatory glucocorticosteroid, e.g. for use in nasal and oral inhalation. Examples of glucocorticosteroids which may be used in the present invention include betamethasone, fluticasone (e.g. as propionate), budesonide, tipredane, dexamethasone, beclomethasone (e.g. as dipropionate), prednisolone, fluocinolone, triamcinolone (e.g. as acetonide), momethasone (e.g. as furoate), rofleponide (e.g. as palmitate), flumethasone, flunisolide, ciclesonide, deflazacort, cortivazol, 16α, 17α-butylidenedioxy-6α,9α-difluoro-11β,21-dihydroxy-pregna-1,4-diene-3,20-dione; 6α,9α-difluoro-11β-hydroxy-16α,17α-butylidenedioxy-17β-methylthioandrosta-4-ene-3-one; 16α,17α-butylidenedioxy-6α,9α-difluoro-11β-hydroxy-3-oxo-androsta-1,4-diene-17β-carbothioic acid S-methyl ester; methyl 9α-chloro-6α-fluoro-11β-hydroxy-16α-methyl-3-oxo-17α-propionyloxy-6α,9α-difluoro-11β-hydroxy-16α-methyl-3-oxo-17α-propionyloxy-androsta-1,4-dien-17β-carbothioic acid S-(2-oxo-tetrahydrofuran-3-yl) ester; optionally in their pure isomeric forms (where such forms exist) and/or in the form of their esters, acetals or salts, where applicable. Suitably, use is made of momethasone furoate, beclomethasone dipropionate or fluticasone propionate or glucocorticosteroids with an asymmetric acetal structure, i.e. comprising 16α,17α-butylidenedioxy, such as budesonide, rofleponide or rofleponide palmitate. Preferably, use is made of budesonide, rofleponide or rofleponide palmitate and most preferably of budesonide.

The glucocorticosteroid is preferably used in the form of a finely divided, e.g. micronized, powder, particularly in the form of finely divided particles having a mass median diameter of less than 10 μm, more preferably less than 5 μm. The glucocorticosteroid may alternatively be in an ultra fine form, e.g. having a mass median diameter of less than 1.0 μm. The finely divided particles may be produced by conventional techniques known per se. e.g. by micronization or by direct precipitation. Information about micronization can be found e.g. in "The Theory and Practice of Industrial Pharmacy", Lachman, Liebermann and Klang, $2^{nd}$ Ed., 1976, Lea & Febiger, Philadelphia, USA.

The temperature, time, batch size and type of sterilizer used will be interdependent. Thus generally the higher the temperature used in the process according to the invention, the less time is required to sterilize the glucocorticosteroid. The process is preferably carried out for no more than 8 hours, e.g. from 1 to 8 hours, when the temperature is greater than about 110° C., more preferably no more than 4 hours. At a temperature of about 120° C. the process is preferably carried out for no more than 4 hours, e.g. from 1 to 4 hours. more preferably no more than 2 hours, e.g. from 1 to 2 hours.

At temperatures of from about 110° C. up to 130° C., a batch of 50 g of glucocorticosteroid may suitably be heat treated from 1 to 4 hours. If desired sub-batches, e.g. of 4×50 g, may be used.

The present process may be carried out such that it results in a more than log 4 reduction in the amount of heat resistant spores. The process of the present invention is suitably carried out such that it results in a log 6 reduction in the amount of heat resistant spores. The present process is preferably carried out such that it results in a more than log 6 reduction, and more preferably such that it results in a more than log 7 reduction in the amount of heat resistant spores.

A different way of characterizing the efficiency of a sterilizing process is by using the D value. The D value, also known as the $D_T$ value, is the time (in minutes) required to reduce ("kill") a standardized population of spores by 90% or 1 log cycle, i.e. to a survival fraction of 1/10, at a specific temperature T (in ° C.).

The present process may be carried out such that the D value is less than about 240 min at the preselected temperature T, wherein T is in the range of from 100 to 130° C. The process of the present invention is suitably carried out such that the D value is less than 150 min at the preselected temperature T. Preferably, the process of the present invention is carried out such that the D value is less than 90 min at the preselected temperature T, and more preferably such that the D value is less than 30 min at the preselected temperature T. T is suitably 100, 110, 120 or 130° C.

The sterilization process is desirably carried out in such a manner that all parts of the bulk of the glucocorticosteroid reaches, and is maintained within, the desired temperature for the desired time.

The present process may be carried out batch wise or continuously, preferably batch wise.

The glucocorticosteroid starting material for the process, which material may be in finely divided form, is suitably substantially dry, i.e. containing less than about 1% (w/w) of water. Preferably, the starting material for the process contains less than 0.5% (w/w) of water, and more preferably less than 0.3% (w/w) of water.

The glucocorticosteroid starting material for the process suitably has a bioburden of less than 50 CFU (colony forming units) per gram. The glucocorticosteroid starting material for the process preferably has a bioburden of less than 10 CFU per gram, more preferably of less than 1 CFU per gram.

According to the invention there is further provided a sterile glucocorticosteroid (e.g. budesonide), suitably dry and preferably in the form of finely divided particles, e.g. having a mass median diameter of less than 10 μm, and more preferably less than 5 μm.

By the term "sterile" we mean a product which meets the criteria of sterility according to the US Pharmacopoeia 23/NF18, 1995, pp. 1686-1690 and 1963-1975, and which provides a therapeutically acceptable glucocorticosteroid and formulations thereof. Further regulations for sterility of the final product include the European Pharmacopoeia (Ph. Eur. 1998, Chapters 2.6.1 and 5.1.1), the British Pharmacopoeia (BP 1993, Appendix XVI A, p. A180 and Appendix XVIII A, p. A 184) and the Japanese Pharmacopoeia (JP, $13^{th}$ ed., pp. 69-71 and 181-182). Preferably, the therapeutically acceptable glucocorticosteroid and formulations thereof have been produced by a method which provides assurance of sterility according to the US Pharmacopoeia 23/NF18, 1995, pp. 1686-1690 and 1963-1975.

The glucocorticosteroid according to the invention will essentially maintain the same pharmacological activity and physico-chemical properties/its chemical purity and physical form as the starting material from which it is prepared, i.e. the degradation, and especially the chemical degradation, caused by the present sterilization process will be limited.

The glucocorticosteroid according to the invention is preferably at least 98.5% by weight pure, more preferably at least 99% by weight pure, and most preferably at least 99.2% by weight pure.

The invention further provides a sterile glucocorticosteroid, preferably an anti-inflammatory glucocorticosteroid, more preferably budesonide, rofleponide or rofleponide palmitate, and most preferably budesonide, for use in the treatment of an allergic and/or inflammatory condition of the nose or lungs, e.g. chronic obstructive pulmonary disease (COPD), rhinitis or asthma. The invention also provides the use of such a sterile glucocorticosteroid, preferably an anti-inflammatory glucocorticosteroid, more preferably budesonide, in the manufacture of a medicament (preferably a sterile medicament) for use in the treatment of such conditions.

According to the invention there is further provided a sterile pharmaceutical formulation comprising a glucocorticosteroid in an aqueous suspension, wherein the glucocorticosteroid is preferably a sterile finely divided glucocorticosteroid, such as budesonide.

According to the invention there is also provided a sterile pharmaceutical formulation comprising a glucocorticosteroid and one or more pharmaceutically acceptable additives, to diluents or carriers. Examples of such additives include surfactants, pH regulating agents, chelating agents, agents rendering the suspension isotonic and thickening agents.

To obtain an efficient dispersion of the glucocorticosteroid particles in the suspension, a surfactant may be used, optionally in combination with e.g., lecithin. The surfactants may also function as stabilizing agents in the formulations according to the present invention. Examples of suitable surfactants include non-ionic surfactants of the alkyl aryl polyether alcohol type, specifically tyloxapol —a polymer of 4-(1,1,3,3-tetramethylbutyl)phenol with ethylene oxide and formaldehyde. Further suitable surfactants include sorbitan derivatives, e.g. polyoxyethylene sorbitan fatty acid esters, preferably of the polysorbate or Tween™ groups, more preferably polysorbate 80 or polyoxyethylene 20 sorbitan monooleate (Tween™ 80). Suitable surfactants also include polyoxyethylene ethers, especially polyoxyethylene alkyl ethers, preferably pentaethyleneglycol mono n-dodecylether or $C_{12}E_5$. Further suitable surfactants include poloxamers, polyoxyethylene castor oil derivatives, polyvinylalcohol and block copolymers of polyethyleneoxides, polypropyleneoxides, polybutyleneoxides and polyethyleneglycols (PEGs) or mixtures of any of these. Further suitable surfactants include polyethylene glycol derivatives, especially polyethylene glycol 660 hydroxystearate or Solutol™ HS 15, povidone, polyvinylpyrrolidone (PVP) and polyethyleneglycols (PEGs).

The surfactant may be present at about 0.002 to 2% w/w of the formulation. We prefer the polyoxyethylene sorbitan fatty acid esters to be present at about 0.005 to 0.5% w/w, poloxamers at about 0.01 to 2% w/w, and polyoxyethylene alkyl ethers or thepolyoxy-ethylene castor oil derivatives at about 0.01 to 1.0% w/w of the formulation.

The pH of the suspension may be adjusted as required. Examples of suitable pH regulating agents are weak organic acids, e.g. citric acid, strong mineral acids, e.g. hydrochloric acid, and strong alkaline agents. e.g. NaOH. Alternatively, the pH of the system can be adjusted by balancing the acid and salt forms of buffers such as citric acid, sodium citrate, acetic acid, sodium acetate and sodium phosphate. We prefer the formulations intended for inhalation to have a pH in the range of from about 3.5 to about 6.0, more preferably from 4.0 to 5.0, and most preferably from 4.2 to 4.8.

We also prefer the formulation to contain a suitable chelating agent, e.g. disodium edetate (EDTA). The chelating agent may be present at about 0.005 to 0.1% w/w of the formulation.

Agents which make the suspension isotonic may be added. Examples are dextrose, glycerol, mannitol, sodium chloride, potassium chloride and sodium bromide.

In order to form a stable suspension with a minimal tendency to agglomerate or form a sediment, a thickening agent may be included in the formulation. Examples of suitable thickening agents are cellulose derivatives, suitably cellulose ethers, or microcrystalline cellulose. Preferred cellulose ethers include ethylcellulose, ethylmethylcellulose, hydroxyethylcellulose, hydroxyethylmethylcellulose, hydroxyethylethylcellulose, methylcellulose, hydroxymethylcellulose, hydroxypropylcellulose, hydroxypropylmethylcellulose and carboxymethylcellulose (CMC), e.g. the sodium salt thereof. Suitable thickening agents also include cyclodextrin and dextrin. Suitable thickening agents further include xanthan gum, guar gum and carbomer. Preferred thickening agents in the formulations of the invention are povidone, polyvinylpyrrolidone (PVP) and polyethyleneglycols (PEGs).

The thickening agent may be present at about 0.1 to 3.0% w/w of the formulation. Preferably microcrystalline cellulose and sodium carboxymethyl cellulose (CMC) are present at about 0.5 to 2.5%, xanthan gum at about 0.3 to 3%, carbomer at about 0.1 to 2%, guar gum at about 0.3 to 2% and hydroxypropyl methyl cellulose at about 0.5 to 3.0%, w/w of the formulation.

In the suspension the active constituent, e.g. budesonide, is present as small particles, where at least 90% of the small particles have a mass median diameter (MMD) of less than 20 µm, suitably at least 80% less than 10 µm, preferably at least 70% less than 7 µm and most preferably at least 60% less than 4 µm.

We prefer the suspension to contain from about 0.05 to about 20 mg/ml of the glucocorticosteroid. More preferably the suspension contains from 0.08 to 10 mg/ml of the glucocorticosteroid and most preferably from 0.1 to 5 mg/ml of the glucocorticosteroid.

A sterile pharmaceutical formulation comprising a glucocorticosteroid, such as finely divided budesonide, rofleponide or rofleponide palmitate, sterilized according to the present process, can be prepared by mixing the sterilized glucocorticosteroid with any suitable additional ingredient, e.g. a surfactant, a pH regulating or chelating agent, an agent rendering the suspension isotonic or a thickening agent. All components, other than the glucocorticosteroid, can be produced by sterile filtration of their aqueous solutions. The resulting sterile suspension may be stored under an over pressure of a sterile and inert gas, e.g. nitrogen or argon, and should be filled under aseptic conditions into pre-sterilized containers to produce a sterile pharmaceutical product, e.g. using a blow/fill/seal system.

The invention further provides a method for treatment of an inflammatory condition of the nose or lungs by administering to a mammal, especially a human being, suffering from such a condition a therapeutically effective amount of a sterile glucocorticosteroid or a sterile formulation containing a glucocorticosteroid, preferably a sterile formulation containing a sterile glucocorticosteroid produced according to the present invention. More specifically, the invention provides a method for treatment of chronic obstructive pulmonary disease (COPD), rhinitis, asthma or other allergic and/or inflammatory conditions by administering to a mammal, especially a human being, suffering from such a condition a therapeutically effective amount of a sterile glucocorticosteroid or a sterile formulation containing a glucocorticosteroid, preferably a sterile formulation containing a sterile glucocorticosteroid produced according to the present invention.

EXAMPLES

The invention is illustrated by reference to the following Examples which are not intended to limit the invention.

Example 1

Experiments were carried out to determine the effect of heat treatment upon the chemical purity and physical form of samples of micronized budesonide.

Nine 50 g batches of micronized budesonide (sample nos. 2-10 in Table 1 below) were subjected to the heat treatment shown in Table 1 in a dry sterilizer, Lytzen model CB 1200. Sample 1 was not subjected to such treatment and was used as the reference sample. After the treatment the samples were analyzed for chemical and physical properties.

TABLE 1

| No. | 1 | 2 | 3 | 4 | 5 | 6 | 7 | 8 | 9 | 10 |
|---|---|---|---|---|---|---|---|---|---|---|
| Temp/° C. | — | 100 | 100 | 100 | 110 | 110 | 110 | 120 | 120 | 120 |
| Time/hours | 0 | 4 | 6 | 10 | 2 | 4 | 10 | 1 | 2 | 4 |
| Size/µm | 2.0 | 2.2 | 2.2 | 2.2 | 2.2 | 2.2 | 2.3 | 2.2 | 2.2 | 2.3 |
| Size range (10-90%)/µm | 2.6 | 2.5 | 2.5 | 2.5 | 2.5 | 2.5 | 2.5 | 2.5 | 2.5 | 2.5 |
| Epimer A/% by wt | 48.8 | 48.8 | 48.7 | 48.7 | 48.7 | 48.8 | 48.7 | 48.7 | 48.7 | 48.7 |
| Budesonide content/% by wt | 99.4 | 99.3 | 99.3 | 99.2 | 99.2 | 99.3 | 98.9 | 99.2 | 99.2 | 99.0 |
| Total of known foreign steroids | 0.13 | 0.14 | 0.16 | 0.15 | 0.16 | 0.15 | 0.18 | 0.14 | 0.15 | 0.17 |
| Total of unknown foreign steroids | 0.04 | 0.04 | 0.05 | 0.05 | 0.04 | 0.08 | 0.18 | 0.04 | 0.07 | 0.16 |

After the heat treatment there was no change in the Brunauer, Emett and Teller (BET) surface value (as measured using a Micrometrics Gemini 2375 device; see also British Standard 4359 (1969) part 1) of the budesonide or in its X-ray diffraction pattern for each sample compared to sample 1. The size for each sample was measured as the mass median diameter (MMD) using a Coulter counter.

Example 2

The sterilization of budesonide was compared with that of calcium stearate.

Samples of 0.5 g of budesonide and of 0.5 g of calcium stearate were each inoculated with 0.1 ml of a Steris *Bacillus subtilis* (*globigii*) (Lot#LG126B) spore suspension containing $1.5 \times 10^7$ spores. Each sample was subjected to a temperature of 110° C. for 3 hours and 10 min in a Baxter Constant Temperature Oven using the same technique as in Example 1. The spore population of the samples was measured and the results obtained are shown below in Table 2.

TABLE 2

| Compound | Before | After |
|---|---|---|
| Calcium stearate | $1.5 \times 10^7$ spores | $3.3 \times 10^6$ spores |
| Budesonide | $1.5 \times 10^7$ spores | <10 spores |

As a result of the heat treatment, a spore log reduction of greater than 6.2 was obtained in the inoculated sample of budesonide, whereas the log reduction was less than 0.7 in the inoculated sample of calcium stearate.

Example 3

Tests were performed to evaluate the heat resistance of various naturally occurring microorganisms.

Samples of 0.5 g of budesonide powder were each inoculated with approximately $10^2$-$10^3$ viable ATCC microorganisms in 120 ml open-ended polypropylene container. Each sample was subjected to a temperature of 110° C. for 3 hours and 10 min. The microorganism population of the samples was measured before and after heat treatment and the results obtained are shown below in Table 3.

TABLE 3

| Microorganism | Before | After |
|---|---|---|
| E. coli | 450 | 0 |
| B. subtilis ATCC 6633 | 300 | 0 |
| Salmonella typhi | 270 | 0 |
| C. albicans | 780 | 0 |
| A. niger | 260 | 0 |
| M. luteus | 300 | 0 |
| S. epidermidis | 240 | 0 |
| C. sporegenes | 160 | 0 |
| Ps. Aeruginosa | 350 | 0 |
| B. subtilis ATCC 6633 | $1.2 \times 10^5$ | $1^1$ |

[1] A singular *bacillus* species was found, verified by Gram stain in the $10^0$ dilution plate.

As is evident from Table 3, heat treatment of budesonide at 110° for 3 hours and 10 min, is an effective sterilizing method for a substantial variety of microorganisms.

Example 4

A formulation comprising finely divided budesonide sterilized by the method of Example 2, and meeting the criteria of sterility according to the US Pharmacopoeia 23/NF18, 1995, was prepared by mixing the following ingredients:

TABLE 4

| Micronized budesonide | 0.125 mg |
| Disodium edetate | 0.1 mg |
| Sodium chloride | 8.5 mg |
| Polysorbate 80 | 0.2 mg |
| Anhydrous citric acid | 0.28 mg |

TABLE 4-continued

| | |
|---|---|
| Sodium citrate | 0.5 mg |
| Purified water | to 1 ml |

All the components, other than the budesonide, were produced by sterile filtration of their aqueous solutions and an appropriate volume of the resulting suspension (about 2 ml) was filled under aseptic conditions into pre-sterilized 5 ml containers to produce a sterile product.

The resulting suspension may be stored under an overpressure of sterile nitrogen and may be filled into containers using a blow/fill/seal system.

Example 5

A sterile formulation comprising finely divided budesonide sterilized by the method of Example 2, can be prepared by mixing the following ingredients:

TABLE 5

| | |
|---|---|
| Micronized budesonide | 2-3 mg |
| Disodium edetate | 0.1 mg |
| Sodium chloride | 8.5 mg |
| Stabilizing agent | 0.02-2 mg |
| Anhydrous citric acid | 0.28 mg |
| Sodium citrate | 0.5 mg |
| Purified water | to 1 ml |

All the components, other than the budesonide, can be produced by sterile filtration of their aqueous solutions and an appropriate volume of the resulting suspension (about 2 ml) filled under aseptic conditions into pre-sterilized 5 ml containers to produce a sterile product.

The resulting suspension may be stored under an overpressure of sterile nitrogen and may be filled into containers using a blow/fill/seal system.

Example 6

5 g of micronized budesonide was inoculated with approximately 2 ml of a spore suspension of *Bacillus subtilis*.

The substance and the spore suspension were mixed and dried for approximately 3 hours at 55° C. The inoculated and dried budesonide was mixed with 20-40 g of non-inoculated micronized budesonide.

5 g portions of this sample were heat treated at 100° C., 110° C. or 120° C. in a Heraeus ST 5060 heating apparatus. A 1 g sample was withdrawn after various heating times at the respective heating temperatures. Each such 1 g sample was transferred to 10 ml of dilution medium pH 7.2. Appropriate dilutions were made in 0.1% Peptone Aqueous solution and the number of spores/g were determined by a pour plate technique according to US Pharmacopoeia 23/NF18, 1995, pp. 1681-1686, especially p. 1684.

The number of spores before heat treatment were determined in samples heated at 80° C. for 10 min in order to kill the vegetative cells.

The results are shown in Table 6. where the $D_T$ value is the amount of time in minutes required to obtain a log 1 reduction in the number of spores before and after heat treatment at the temperature T (in ° C.).

TABLE 6

| | Heating at 100° C. | | | |
|---|---|---|---|---|
| | 80° C. | Heating time at 100° C. | | |
| | 10 min | 15 min | 45 min | 75 min |
| spores/g | $6.5 \times 10^6$ | $4.8 \times 10^3$ | $7.1 \times 10^2$ | $1.7 \times 10^2$ |
| log spores/g | 6.81 | 3.68 | 2.85 | 2.23 |
| | Heating at 110° C.. | | | |
| | 80° C. | Heating time at 110° C. | | |
| | 10 min | 5 min | 15 min | 20 min |
| spores/g | $2 \times 10^6$ | $2.08 \times 10^4$ | $9.25 \times 10^2$ | $3.55 \times 10^2$ |
| log spores/g | 6.20 | 4.32 | 2.97 | 2.55 |
| | Heating at 120° C. | | | |
| | 80° C. | Heating time at 120° C. | | |
| | 10 min | 4 min | 6 min | 8 min |
| spores/g | $1.5 \times 10^6$ | $1.9 \times 10^2$ | $5.5 \times 10^1$ | $2 \times 10^1$ |
| log spores/g | 6.19 | 2.28 | 1.74 | 1.30 |

$D_{100}$ = 41.5 min; correlation coefficient = −0.0996 This means that it takes 6 × 41.5 minutes to obtain a log 6 reduction in the number of spores at a temperature of 100° C.
$D_{110}$ = 8.3 min; correlation coefficient = −0.995 This means that it takes 6 × 8.3 minutes to obtain a log 6 reduction in the number of spores at a temperature of 110° C.
$D_{120}$ = 4.1 min; correlation coefficient = −0.998 This means that it takes 6 × 4.1 minutes to obtain a log reduction in the number of spores at a temperature of 120° C.

Example 7

1 g of micronized budesonide, prednisolone and beclomethasone dipropionate and 0.5 g of rofleponide were inoculated with a different spore suspension to the one used in Example 6.

The samples were heat treated at 110° C. A sample was withdrawn after various heating times. The number of spores/g were determined by a pour plate technique according to US Pharmacopoeia 23/NF18, 1995, pp. 1681-1686, especially p. 1684.

From the number of spores before and after heat treatment the log reduction of spores and decimal reduction time (time needed at a specified temperature to reduce the number of microorganisms with one log) was calculated.

The results are shown in Table 7.

TABLE 7

| | Heating at 110° C. |
|---|---|
| Glucocorticosteroid | $D_{110}$ value in min |
| Budesonide | 41 |
| Rofleponide | 9.8 |
| Beclomethasone dipropionate | 72.7 |
| Prednisolone | 73.8 |

Table 7 clearly shows that the present process is very efficient in reducing the number of spores in samples containing glucocorticosteroids. The process is especially efficient with budesonide and rofleponide. In fact analysis conducted on a full 1.0 g sample of rofleponide yielded total kill at very short cycle times ($\geq$5 minutes at 110° C.), where a $D_{110}$ value could not be calculated.

Comparative Example 8

Irradiation

About 3 g of micronized budesonide substance stored in a plastic container, were subjected to irradiation. The substance was exposed to β-irradiation at 2.5 to 25 kGy and γ-irradiation at 8 to 32 kGy. After the exposure the budesonide content and the amount of related substances were determined by liquid chromatography. The chemical stability of budesonide was considered to be the most critical parameter to study.

TABLE 8

Stability of micronized budesonide substance during sterilization by irradiation

| Exposure Intensity (kGy) | Ref. i) | β 2.5 | β 5 | β 10 | β 17 | β 25 | γ 7.8 | γ 31.9 |
|---|---|---|---|---|---|---|---|---|
| Budesonide content (%) | 99.5–99.8 | 99.1 | 98.9 | 98.9 | 98.8 | 98.8 | 97.9 | 95.0 |
| Related substances | | | | | | | | |
| Total of known foreign steroids | 0.13–0.15 | 0.19 | 0.19 | 0.18 | 0.20 | 0.21 | 0.34 | 0.51 |
| Total of unknown foreign steroids | 0.03–0.04 | 0.19 | 0.24 | 0.26 | 0.36 | 0.43 | 0.68 | 1.8 | i) The analysis was done on different days and the reference was analyzed at all occasions From the results in Table 8, it can be seen that the budesonide content decreases in samples exposed to β- and γ-irradiation. Several new degradation products were observed, especially for the γ-irradiated sample. In addition the mass balance for both β- and γ-irradiated samples is poor. The budesonide content has decreased by 0.5–4.6 percent, when exposed to β- or γ-irradiation.

It can be concluded that micronized budesonide can not be satisfactorily sterilized with β- or γ-irradiation, due to significant chemical degradation.

The invention claimed is:

1. A pharmaceutically acceptable, micronized powder composition at least 98.5% by weight of which is pure budesonide or an ester, acetal or salt thereof, wherein the composition meets the criteria of sterility according to the US Pharmacopoeia 23/NF18, 1995, pages 1686–1690 and 1963–1975.

2. The composition of claim 1, wherein at least 98.5% of the composition is pure budesonide.

3. The composition of claim 1, wherein at least 99% by weight of the composition is pure budesonide or an ester, acetal or salt thereof.

4. The composition of claim 1, wherein at least 99.2% by weight of the composition is pure budesonide or an ester, acetal or salt thereof.

5. The composition of claim 1, wherein the composition is in the form of particles having a mass median diameter (MMD) of less than 10 μm.

6. The composition of claim 5, wherein the particles have a MMD of less than 5 μm.

7. The composition of claim 5, wherein the particles have a MMD of less than 1 μm.

8. The composition of claim 5, wherein at least 99% by weight of the composition is pure budesonide or an ester, acetal or salt thereof.

9. The composition of claim 5, wherein at least 99.2% by weight of the composition is pure budesonide or an ester, acetal or salt thereof.

10. The composition of claim 1, wherein the composition is in the form of particles at least 80% of which have a MMD of less than 10 μm.

11. The composition of claim 10, wherein at least 99% by weight of the composition is pure budesonide or an ester, acetal or salt thereof.

12. The composition of claim 10, wherein at least 99.2% by weight of the composition is pure budesonide or an ester, acetal or salt thereof.

13. The composition of claim 10 wherein at least 70% of the particles have a MMD of less than 7 μm.

14. The composition of claim 13, wherein at least 99% by weight of the composition is pure budesonide or an ester, acetal or salt thereof.

15. The composition of claim 13, wherein at least 99.2% by weight of the composition is pure budesonide or an ester, acetal or salt thereof.

16. The composition of claim 10 wherein at least 60% of the particles have a MMD of less than 4 μm.

17. The composition of claim 16, wherein at least 99% by weight of the composition is pure budesonide or an ester, acetal or salt thereof.

18. The composition of claim 16, wherein at least 99.2% by weight of the composition is pure budesonide or an ester, acetal or salt thereof.

19. The composition of claim 1, wherein the budesonide is isomerically pure.

20. The composition of claim 19, wherein the budesonide is in the form of the (22R) diastereoisomer.

21. A method for the treatment of an inflammatory condition, the method comprising administering to a mammal suffering from such a condition a therapeutically effective amount of the composition of claim 1.

22. A method for the treatment of an inflammatory condition, the method comprising administering to a mammal suffering from such a condition a therapeutically effective amount of the composition of claim 2.

23. The method of claim 21, wherein the mammal is a human being.

24. A method for the treatment of chronic obstructive pulmonary disease (COPD), the method comprising administering to a mammal suffering from COPD a therapeutically effective amount of the composition of claim 1.

25. A method for the treatment of COPD, the method comprising administering to a mammal suffering from COPD a therapeutically effective amount of the composition of claim 2.

26. The method of claim 24, wherein the mammal is a human being.

27. A method for the treatment of rhinitis, the method comprising administering to a mammal suffering from rhinitis a therapeutically effective amount of the composition of claim 1.

28. A method for the treatment of rhinitis, the method comprising administering to a mammal suffering from rhinitis a therapeutically effective amount of the composition of claim 2.

29. The method of claim 27, wherein the mammal is a human being.

30. A method for the treatment of asthma, the method comprising administering to a mammal suffering from asthma a therapeutically effective amount of the composition of claim 1.

31. A method for the treatment of asthma, the method comprising administering to a mammal suffering from asthma a therapeutically effective amount of the composition of claim 2.

32. The method of claim 30, wherein the mammal is a human being.

33. A method for the treatment of an allergic condition, the method comprising administering to a mammal suffering from an allergic condition a therapeutically effective amount of the composition of claim 1.

34. A method for the treatment of an allergic condition, the method comprising administering to a mammal suffering from an allergic condition a therapeutically effective amount of the composition of claim 2.

35. The method of claim 33, wherein the mammal is a human being.

36. The method of claim 21, wherein the budesonide is isomerically pure.

37. The method of claim 36, wherein the budesonide is in the form of the (22R) diastereoisomer.

38. A pharmaceutically acceptable, sterilized powder composition at least 98.5% by weight of which is pure budesonide or an ester, acetal or salt thereof, wherein the sterilized powder composition was produced by sterilization of viable-microorganism-containing particles of budesonide or an ester, acetal or salt thereof.

39. The composition of claim 38, wherein at least 98.5% by weight of the composition is pure budesonide.

40. The composition of claim 38, at least 99% by weight of which is pure budesonide or an ester, acetal or salt thereof.

41. The composition of claim 38, at least 99.2% by weight of which is pure budesonide or an ester, acetal or salt thereof.

42. The composition of claim 41, wherein the sterilization was accomplished by a method comprising heat sterilization.

43. The composition of claim 42, wherein the heat sterilization was carried out in air.

44. The composition of claim 42, wherein the heat sterilization was carried out under an inert gas atmosphere.

45. The composition of claim 42, wherein the heat sterilization was accomplished at a temperature of 100 to 130° C.

46. The composition of claim 42, wherein the heat sterilization was accomplished at a temperature of 110 to 120° C.

47. The composition of claim 42, wherein the heat sterilization was accomplished at a temperature of 110° C.

48. The composition of claim 38, wherein the budesonide is isomerically pure.

49. The composition of claim 48, wherein the budesonide is in the form of the (22R) diastereoisomer.

50. A pharmaceutically acceptable suspension consisting of a micronized powder composition at least 98.5% by weight of which is pure budesonide or an ester, acetal or salt thereof, suspended in an aqueous solution, wherein the suspension meets the criteria of sterility according to the US Pharmacopoeia 23/NF18, 1995, pages 1686-1690 and 1963-1975.

51. The pharmaceutically acceptable suspension of claim 50, wherein at least 98.5% by weight of the micronized powder composition is pure budesonide.

52. The pharmaceutically acceptable suspension of claim 50, wherein at least 99% by weight of the micronized powder composition is pure budesonide or an ester, acetal or salt thereof.

53. The pharmaceutically acceptable suspension of claim 50, wherein at least 99.2% by weight of the micronized powder composition is pure budesonide or an ester, acetal or salt thereof.

54. The suspension of claim 50, wherein one or more pharmaceutically acceptable ingredients selected from the group consisting of surfactants, pH regulating agents, chelating agents, agents that make the suspension isotonic, and thickening agents are dissolved in the aqueous solution.

55. The suspension of claim 54 comprising a surfactant that is a non-ionic surfactant, a sorbitan derivative, a polyoxyethylene ether, a polyoxyethylene castor oil derivative, or polyoxyethylene glycol, dissolved in the aqueous solution.

56. The suspension of claim 55, wherein the surfactant is present at about 0.002 to 2% w/w of the suspension.

57. The suspension of claim 55, wherein the surfactant is tyloxapol; polysorbate 80; or polyethylene glycol 660 hydroxystearate.

58. The suspension of claim 54 comprising a pH regulating agent that is a weak organic acid, mineral acid, strong alkaline agent or buffer.

59. The suspension of claim 58, wherein the pH regulating agent is citric acid, hydrochloric acid, NaOH, or sodium citrate.

60. The suspension of claim 58, wherein the suspension has a pH of about 3.5 to 6.0.

61. The suspension of claim 58, wherein the suspension has a pH of about 4.0 to 6.0.

62. The suspension of claim 58, wherein the suspension has a pH of about 4.2 to 4.8.

63. The suspension of claim 54, wherein a chelating agent is present at about 0.005 to 0.1% w/w of the suspension.

64. The suspension of claim 63, wherein the chelating agent is disodium edetate (EDTA).

65. The suspension of claim 54 comprising dextrose, glycerol, mannitol, or sodium chloride in an amount to make the solution isotonic.

66. The suspension of claim 54, wherein the aqueous solution comprises a thickening agent constituting about 0.1 to 3.0% w/w of the suspension.

67. The suspension of claim 66, wherein the thickening agent is ethyl cellulose, ethylmethylcellulose, cyclodextrin, dextrin, xanthan gum, providone, polyvinyiprovidone (PVP) or polyethyleneglycol (PEG).

68. A method for the treatment of an inflammatory condition, the method comprising administering to a mammal suffering from such a condition a therapeutically effective amount of the suspension of claim 50.

69. A method for the treatment of an inflammatory condition, the method comprising administering to a mammal suffering from such a condition a therapeutically effective amount of the suspension of claim 51.

70. The method of claim 68, wherein the mammal is a human being.

71. A method for the treatment of COPD, the method comprising administering to a mammal suffering from COPD a therapeutically effective amount of the suspension of claim 50.

72. A method for the treatment of COPD, the method comprising administering to a mammal suffering from COPD a therapeutically effective amount of the suspension of claim 51.

73. The method of claim 71, wherein the mammal is a human being.

74. A method for the treatment of rhinitis, the method comprising administering to a mammal suffering from rhinitis a therapeutically effective amount of the suspension of claim 50.

75. A method for the treatment of rhinitis, the method comprising administering to a mammal suffering from rhinitis a therapeutically effective amount of the suspension of claim 51.

76. The method of claim 74, wherein the mammal is a human being.

77. A method for the treatment of asthma, the method comprising administering to a mammal suffering from asthma a therapeutically effective amount of the suspension of claim 50.

78. A method for the treatment of asthma, the method comprising administering to a mammal suffering from asthma a therapeutically effective amount of the suspension of claim 51.

79. The method of claim 77, wherein the mammal is a human being.

80. A method for the treatment of an allergic condition, the method comprising administering to a mammal suffering from an allergic condition a therapeutically effective amount of the suspension of claim 50.

81. A method for the treatment of an allergic condition, the method comprising administering to a mammal suffering from an allergic condition a therapeutically effective amount of the suspension of claim 51.

82. The method of claim 80, wherein the mammal is a human being.

83. A pharmaceutically acceptable suspension consisting of a sterilized powder composition at least 98.5% by weight of which is pure budesonide or an ester acetal or salt thereof, suspended in an aqueous solution, wherein the sterilized powder composition was produced by sterilization of viable-microorganism-containing particles of budesonide or an ester, acetal or salt thereof, wherein the suspension meets the criteria of sterility according to the US Pharmacopoeia 23/NF18, 1995, pages 1686-1690 and 1963-1975.

84. The pharmaceutically acceptable suspension of claim 83, wherein at least 98.5% by weight of the powder composition is pure budesonide.

85. The pharmaceutically acceptable suspension of claim 83 wherein at least 99% by weight of the powder composition is pure budesonide or an ester, acetal or salt thereof.

\* \* \* \* \*

UNITED STATES PATENT AND TRADEMARK OFFICE
CERTIFICATE OF CORRECTION

| | |
|---|---|
| PATENT NO. | : 7,524,834 B2 |
| APPLICATION NO. | : 09/993669 |
| DATED | : April 28, 2009 |
| INVENTOR(S) | : Ann-Kristin Karlsson et al. |

Page 1 of 1

It is certified that error appears in the above-identified patent and that said Letters Patent is hereby corrected as shown below:

<u>Title page, item [56], U.S. Patent documents:</u>

Delete "Radhakrishman et al." and replace with --Radhakrishnan et al.--

<u>Title page, under item [56], Other Publications:</u>

Delete "Radolytic" and replace with --Radiolytic--

<u>Column 12, line 16:</u>

In claim 13, insert a comma after "claim 10"

<u>Column 12, line 25:</u>

In claim 16, insert a comma after "claim 10"

<u>Column 14, line 45:</u>

In claim 67, delete "polyvinyiprovidone" and replace with --polyvinylprovidone--

<u>Column 16, line 9:</u>

In claim 83, insert a comma after "ester"

<u>Column 16, line 21:</u>

In claim 85, insert a comma after "83"

Signed and Sealed this

Twenty-eighth Day of July, 2009

JOHN DOLL
*Acting Director of the United States Patent and Trademark Office*